(12) United States Patent
Tripathi et al.

(10) Patent No.: US 10,538,551 B2
(45) Date of Patent: Jan. 21, 2020

(54) PROCESS FOR PREPARATION OF CORTICOSTEROIDS

(71) Applicant: CORAL DRUGS PVT. LTD., Delhi (IN)

(72) Inventors: Vinayak Tripathi, Delhi (IN); Rajesh Kumar, Delhi (IN); Rohit Bhuwania, Delhi (IN); Binay Kumar Bhuwania, Delhi (IN)

(73) Assignee: CORAL DRUGS PVT. LTD., Delhi (IN)

( * ) Notice: Subject to any disclaimer, the term of this patent is extended or adjusted under 35 U.S.C. 154(b) by 0 days.

(21) Appl. No.: 16/327,972

(22) PCT Filed: Aug. 14, 2017

(86) PCT No.: PCT/IN2017/050347
§ 371 (c)(1),
(2) Date: Feb. 25, 2019

(87) PCT Pub. No.: WO2018/037423
PCT Pub. Date: Mar. 1, 2018

(65) Prior Publication Data
US 2019/0177361 A1  Jun. 13, 2019

(30) Foreign Application Priority Data
Aug. 25, 2016  (IN) .............................. 201611028947

(51) Int. Cl.
*C07J 71/00*   (2006.01)
*C07J 5/00*    (2006.01)
*C07J 13/00*   (2006.01)

(52) U.S. Cl.
CPC ......... *C07J 71/0031* (2013.01); *C07J 5/0092* (2013.01); *C07J 13/005* (2013.01); *C07J 71/0015* (2013.01)

(58) Field of Classification Search
CPC .... C07J 71/0031; C07J 13/005; C07J 5/0092; C07J 71/0015
See application file for complete search history.

(56) References Cited

FOREIGN PATENT DOCUMENTS

WO    WO-2016120891 A1 *  8/2016  ............ C07J 5/0092

* cited by examiner

*Primary Examiner* — Paul A Zucker
(74) *Attorney, Agent, or Firm* — King & Schickli, PLLC

(57) ABSTRACT

The present invention discloses a process for the preparation of pregnadiene derivatives having formula I, their stereoisomer and intermediate thereof. Formula I wherein each substituent is independently, $R_1$ and $R_2$ is hydrogen or $C_1$-$C_8$ straight, branched alkyl chain, saturated or unsaturated cycloalkyl; $R_3$ is hydrogen or wherein $R_5$ represents $C_1$-$C_8$ straight, branched alkyl chain or cycloalkyl; $R_4$ is hydrogen or halogen; $R_6$ is hydrogen or halogen;

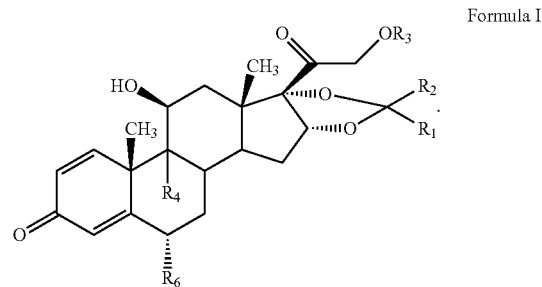

Formula I

8 Claims, No Drawings

PROCESS FOR PREPARATION OF CORTICOSTEROIDS

FIELD OF THE INVENTION

The present invention provides a novel process for the preparation of pregnadiene derivatives

BACKGROUND OF THE INVENTION

Corticosteroids also referred as glucocorticosteroids, glucocorticoids or just steroids influence different body tissues and produce effects on various responsive cells.

Corticosteroids have been found to possess anti-inflammatory and immunosuppressive properties. Several Corticosteroids such as Flunisolide, Fluocinolone acetonide and Fluocinonide are used for treatment of several disorders.

Corticosteroids with significant structural changes and chemical manipulation have been developed. In general, therapeutic corticosteroids have a 21-carbon steroid skeleton; Modifications to this skeleton selectively alter the degree of anti-inflammatory activity and the metabolic consequences and vary the duration of activity and protein-binding affinity of the resultant compound.

Therapeutic corticosteroids are typically classified based on their relative glucocorticoid and mineralocorticoid potency. Such as, acetonides at C-16, C-17 are to improve potency of anti-inflammatory activity of steroids but possess low systematic activity.

Further, halogenations of steroids molecule by 9-halo or 6, 9 dihalo substitutions increase their systematic activity and enhances both glucocorticoid and mineralocorticoid activity of C-16, C-17 substituted acetals, ketals, acetonides, fused ring compounds. For example, Flunisolide is a topical corticosteroid having 6-fluoro and C-16, C-17 acetonide group.

The process for preparation of Corticosteroids having C-16, C-17 substituted acetals, ketals, acetonides, fused ring compounds and halogens at C-6, C-9 or both positions have been disclosed at different instances. However, most of these synthetic procedures involve 6 halo or 6, 9 dihalo, 16a, 17a diols or both as starting materials, which are compounds difficult to prepare handle and purify, the use of toxic solvents or long reaction times are ineffective for large scale synthesis.

For instance, U.S. Pat. No. 3,126,375 discloses a process for the preparation of 6 halo corticoids. The known methods for the preparation of pregnadiene 16, 17acetals, ketals involve the starting material as 6 halo or 6, 9 halo having 16a, 17a diols with aldehydes in the presence of catalyst such as copper sulphate or copper sulphate or perchloricacid solvent which are compounds difficult to prepare and purify and unstable and use of these solvents on large scale require specialized equipments.

WO 03/47329 discloses a method for the preparation of 6α-fluorinated corticosteroids. This application is specific to a 21 ester, 17-hydroxy corticosteroids and does not disclose the various chemicals, starting material, products or reactions and modification thereof. Therefore, the process is not repeatable.

Hence, there is a need to prepare novel Corticosteroidshalogenated at C-6, C-9 or both positions and C-16, C-17 acetals, ketals, acetonides, fused ring compounds using stable, easily available starting materials which can be easily purified, convenient, having high yields, industrially scalable and which does not involve the use of harmful solvents.

OBJECT OF THE INVENTION

An object of the present invention is to provide a novel process for the preparation of pregnadiene derivatives, their stereoisomer and intermediate thereof using stable, easily available and purifiable starting materials without the use of toxic and harmful solvents.

BRIEF DESCRIPTION OF THE INVENTION

The present invention discloses a process for the preparation of pregnadiene derivatives having formula I, their stereoisomer and intermediate thereof.

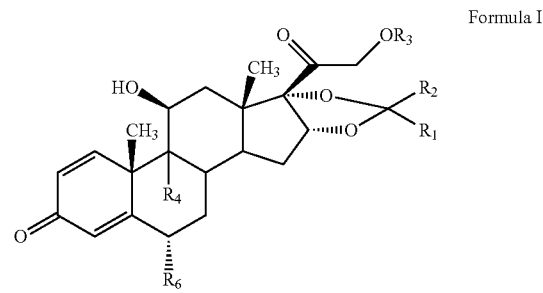

Formula I wherein each substituent is independently,
$R_1$ and $R_2$ is hydrogen or $C_1$-$C_8$ straight, branched alkyl chain, saturated or unsaturated cycloalkyl;
$R_3$ is hydrogen or

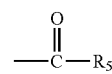

wherein $R_5$ represents $C_1$-$C_8$ straight, branched alkyl chain or cycloalkyl;
$R_4$ is hydrogen or halogen;
$R_6$ is hydrogen or halogen;

The present invention discloses, a novel process for preparing the compounds of formula I;
i. epoxidation of compound of formula II to obtain 9,11-oxido derivative of compound of formula III;
ii. dihydroxylation and optional fluorination of compound of formula III to obtain compound of formula IV with a proviso when $R_6$ is F.
iii. epoxide ring opening of compound of formula IV followed by acetalisation to obtain compound of formula V and optionally, debromination of compound of formula V with a proviso $R_4$ is Br to obtain compound of formula V when R4 is H
iv. deacetylation of compound of Formula V to obtain compound of formula I

DETAILED DESCRIPTION OF THE INVENTION

The present invention discloses a novel process for the preparation of pregnadiene derivatives of formula I, their stereoisomer and intermediate thereof.

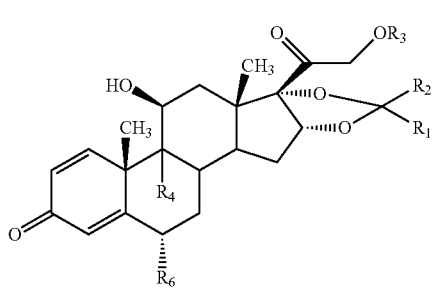

Formula I

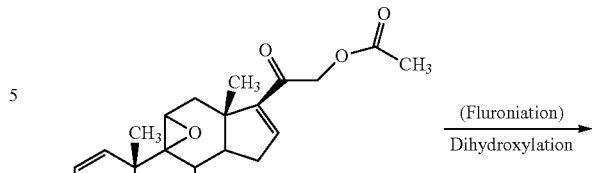

Formula III (Fluroniation)
Dihydroxylation wherein $R_1$ and $R_2$ is independently hydrogen or C1-C8 straight, branched alkyl chain, saturated or unsaturated cycloalkyl;

$R_3$ is hydrogen or

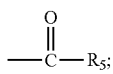

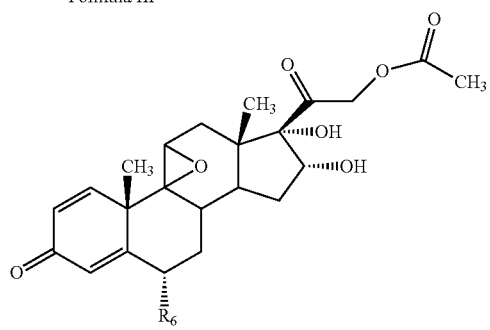

Formula IV $R_5$ represents C1-C8 straight, branched alkyl chain or cycloalkyl;

$R_4$ and $R_6$ is independently hydrogen or halogen;

comprising the steps of:

i. epoxidation of compound of formula II to obtain 9,11-oxido derivative of compound of formula III;

iii. epoxide ring opening of compound of formula IV followed by acetalisation to obtain compound of formula V and optionally, debromination of compound of formula V with a proviso $R_4$ is Br to obtain compound of formula V when R4 is H

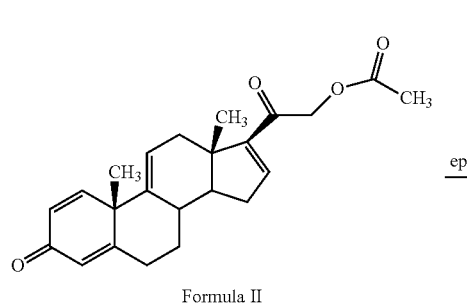

Formula II epoxidation

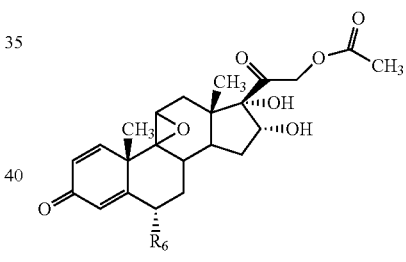

Formula IV epoxide ring
opening/acetalisation (debromination)

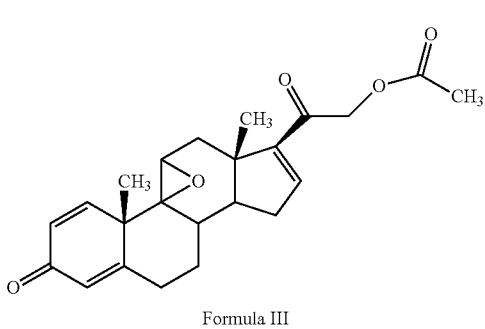

Formula III

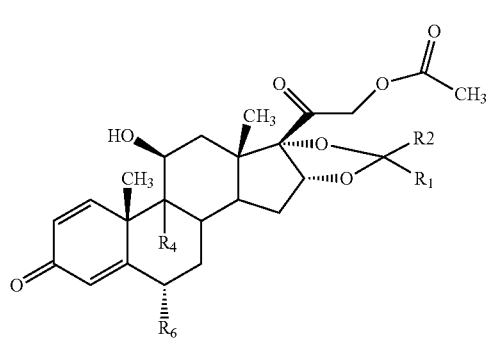

Formula V ii. dihydroxylation and optional fluorination of compound of formula III to obtain compound of formula IV with a proviso when $R_6$ is F.

iv. deacetylation of compound of Formula V to obtain compound of formula I

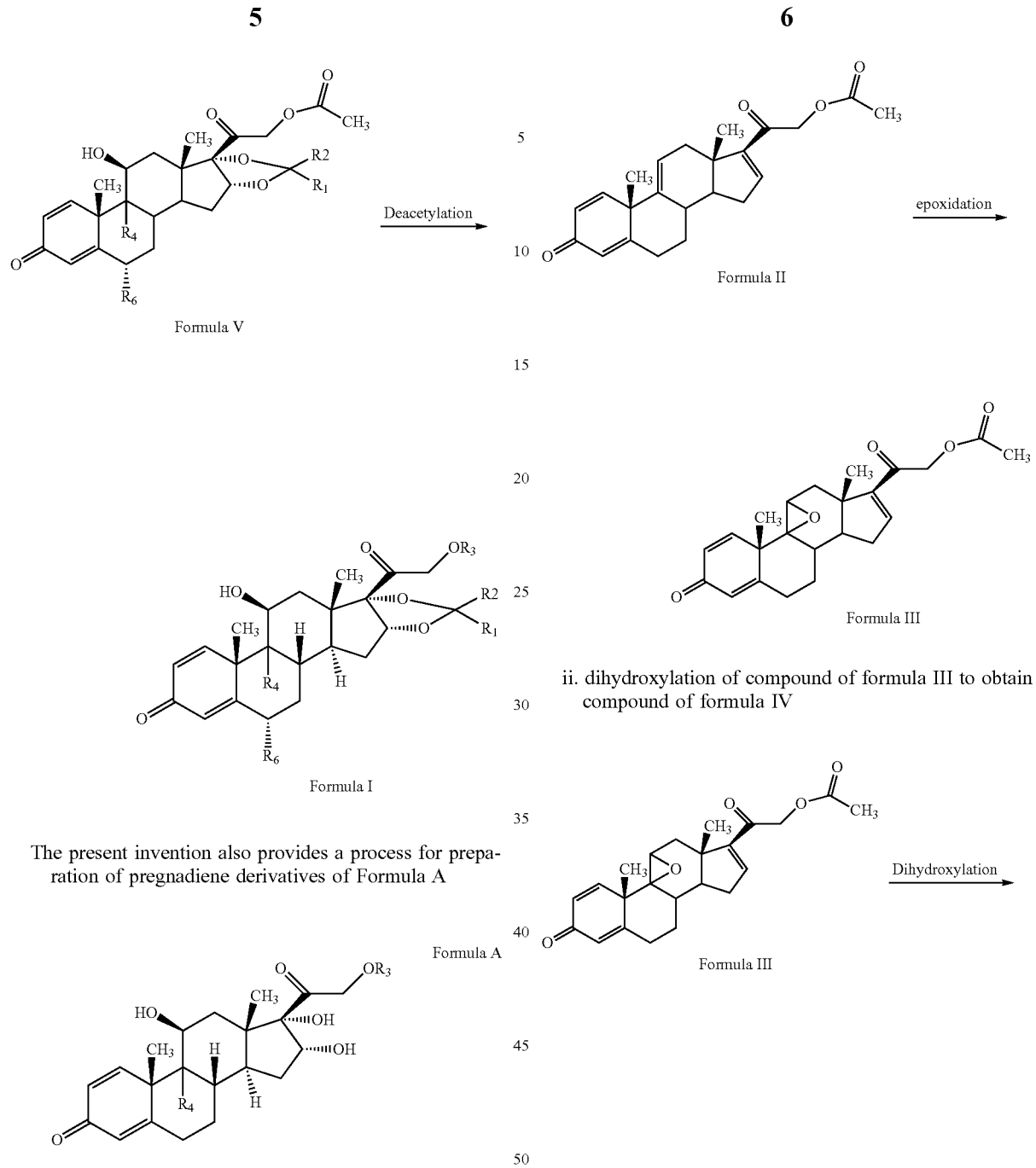

The present invention also provides a process for preparation of pregnadiene derivatives of Formula A wherein R₃ is hydrogen or

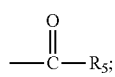

R₅ represents C1-C8 straight, branched alkyl chain or cycloalkyl;

R₄ is halogen;

comprising the steps of:

i. epoxidation of compound of formula II to obtain 9,11-oxido derivative of compound of formula III;

ii. dihydroxylation of compound of formula III to obtain compound of formula IV iii. epoxide ring opening of compound of formula IV followed by acetalisation to obtain compound of formula V

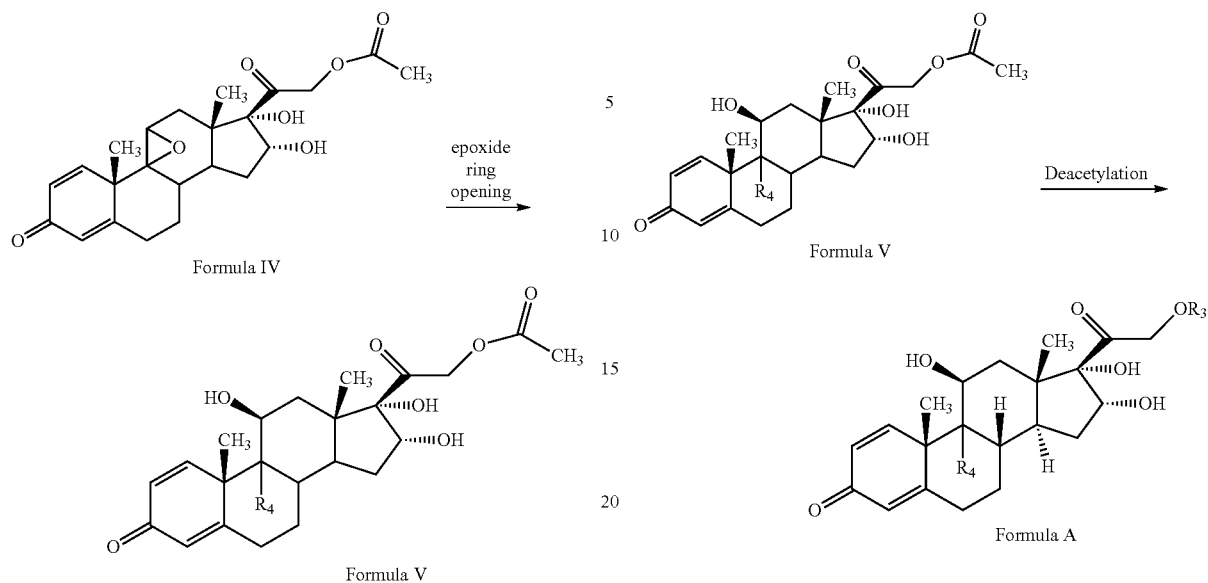

iv. deacetylation of compound of Formula V to obtain compound of formula I

The compounds of formula I, formula V, and formula A may include but are not limited to the following compounds as presented at Table 1:

TABLE 1

| Exemplary compounds of present invention | | |
|---|---|---|
| Structure | Generic name | IUPAC Name |
| | Fluocinolone acetonide | 1S,2S,4R,8S,9S,11S,12R,13S,19S)-12,19-difluoro-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one |
| | Fluocinonide | 6α,9-difluoro-11β,16α,17,21-tetrahydroxypregna-1,4-diene-3,20-dione, cyclic 16,17-acetal with acetone,21-acetate |

TABLE 1-continued

Exemplary compounds of present invention

| Structure | Generic name | IUPAC Name |
|---|---|---|
| 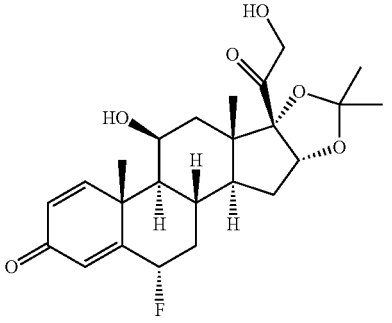 | Flunisolide | 1S,2S,4R,8S,9S,11S,12S,13R,19S)-19-fluoro-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one |
| 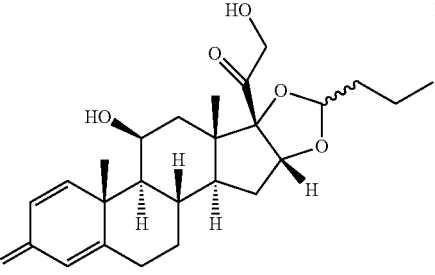 | Budesonide | 16,17-(butylidenebis(oxy))-11,21-dihydroxy-, (11-β,16-α)-pregna-1,4-diene-3,20-dione |
| 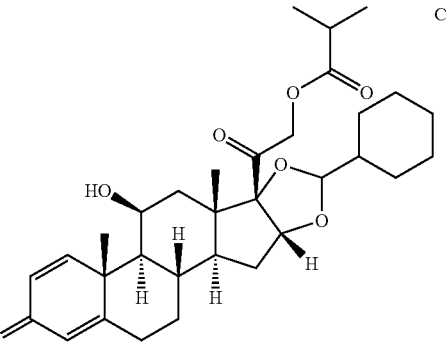 | Ciclesonide | 2-[(1S,2S,4R,8S,9S,11S,12S,13R)-6-cyclohexyl-11-hydroxy-9,13-dimethyl-16-oxo-5,7-dioxapentacyclo [10.8.0.02,9.04,8.013,18]icosa-14,17-dien-8-yl]-2-oxoethyl 2-methylpropanoate. |
| 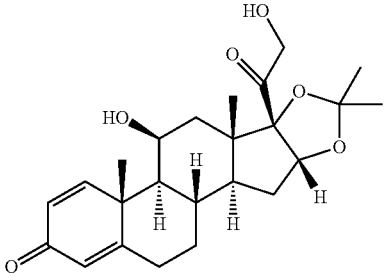 | Desonide | (1S,2S,4R,8S,9S,11S,12S,13R)-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one |
| 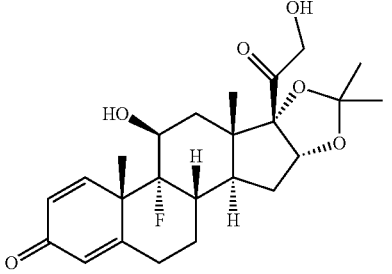 | Triamcinolone acetonide | (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one |

TABLE 1-continued

Exemplary compounds of present invention

| Structure | Generic name | IUPAC Name |
|---|---|---|
| 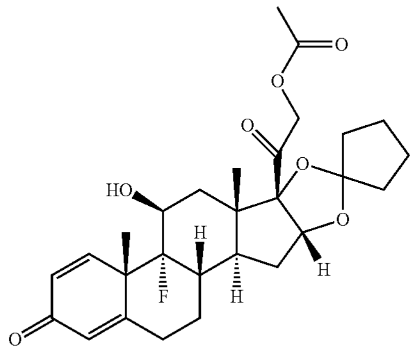 | Amcinonide | 2-[(1S,2S,4R,8S,9S,11S,12R,13S)-12'-fluoro-11'-hydroxy-9',13'-dimethyl-16'-oxo-5',7'-dioxaspiro[cyclopentane-1,6'-pentacyclo[10.8.0.0$^{2,9}$.0$^{4,8}$.0$^{13,18}$]icosane]-14',17'-dien-8'-yl]-2-oxoethyl acetate |
| 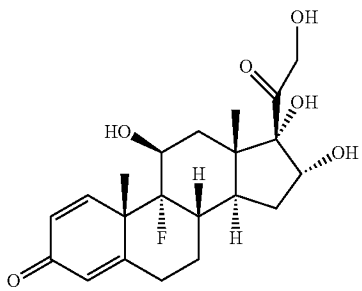 | Triamcinolone | (11β,16α)-9-Fluoro-11,16,17,21-tetrahydroxypregna-1,4-diene-3,20-dione |
| 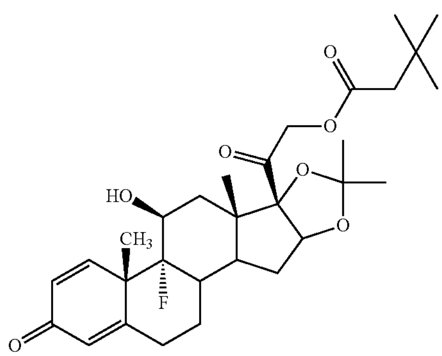 | Triamcinolone hexacetonide | (11β,16α)-21-(3,3-Dimethyl-1-oxobutoxy)-9-fluoro-11-hydroxy-16,17-((1-methylethylidene)bis(oxy))pregna-1,4-diene-3,20-dione |

The process of the present invention is explained at scheme 1.

Scheme 1: Process of the Present Invention

The process of the present invention comprises of the following steps:

i. epoxidation of compound of formula II to obtain 9,11-oxido derivative of compound of formula III;
ii. dihydroxylation and optional fluorination of compound of formula III to obtain compound of formula IV with a proviso when $R_6$ is F.
iii. epoxide ring opening of compound of formula IV followed by acetalisation to obtain compound of formula V and optionally, debromination of compound of formula V with a proviso $R_4$ is Br to obtain compound of formula V when R4 is H
iv. deacetylation of compound of Formula V to obtain compound of formula I The process of the present invention may be suitably started from the compound of formula II, known by its IUPAC name 2-((10S,13S,14S)-10,13-dimethyl-3-oxo-6,7,8,10,12,13,14,15-octahydro-3H-cyclopenta[a]phenanthren-17-yl)-2-oxoethyl acetate and hereinafter referred to as 3TR (formula II).

3TR is suitably epoxidized by an epoxidizing agent. The epoxidizing agents may be selected from the group comprising dibromantin, N-bromoacetaminde or N-bromosuccinimide with Perchloric acid to get bromohydrin, followed by alkali treatment from the group comprising sodium or potassium hydroxide or their carbonates or acetate to form compound of formula (III). The epoxidation of 3TR results in a compound of formula III.

In the present invention, epoxidation of compound of formula (II) is carried out with an epoxidizing agent, selected from group comprising dibromantin, N-bromoacetaminde or N-bromosuccinimide with Perchloric acid, preferably dibromantin with perchloric acid in aqueous acetone to get bromohydrin and epoxidation by alkali from the group comprising sodium or potassium hydroxide or their carbonates or acetate, preferably potassium carbonate to form compound of formula (III).

The process of the present invention involves the fluorination followed by dihydroxylation of the compound of formula III to yield the dihydroxylated fluorinated compound of formula IV. The fluorination of the compound of Formula III may be conducted by suitably reacting the compound of Formula III with a fluorinating agent selected from the group comprising N-fluoro-benzene sulfonamide, N-fluoro-N-chloromethyltrimethylene diamine bistetrafluoroborate, Selectfluor®, 1-fluoropyridinium triflate, 1-fluoropyridinium tetrafluoroborate, or 1-fluoropyridinium pyridine heptafluorodiborateetc, preferably Selectfluor® in presence of a solvent and an acid catalyst. The solvent may be selected from the group comprising acetonitrile, isopropenyl acetate, dichloromethane, dimethyl formamide, diethyl ether, and tetrahydrofuran, preferably isopropenylacetate.

Further, dihydroxylation of the 6-fluoro derivative may be conducted by suitably reacting the compound of Formula III with an oxidizing agent selected from the group comprising potassium permanganate, potassium dichromate, chromic acid, peroxyacids or mixtures thereof, preferably potassium permanganate, formic acid to form compound of formula (IV). Under acidic conditions formic acid promotes oxidation reaction in the formulated product.

In the present invention, compound of formula (III) is fluorinated with a fluorinating agent selected from the group comprising N-fluoro-benzene sulfonamide, N-fluoro-N-chloromethyltrimethylene diamine bistetrafluoroborate, Selectfluor®, 1-fluoropyridinium triflate, 1-fluoropyridinium tetrafluoroborate, or 1-fluoropyridinium pyridine heptafluorodiborate etc, preferably Selectfluor® in presence of a solventin presence of a solvent. The solvent may be selected from the group comprising acetonitrile, dichloromethane, dimethyl formamide, diethyl ether, and tetrahydrofuran followed by dihydroxylation with an oxidizing agent selected from the group comprising potassium permanganate, potassium dichromate, chromic acid, peroxyacids or mixtures thereof, preferably potassium permanganate, formic acid to form compound of formula (IV). Under acidic conditions formic acid promotes oxidation reaction in the formulated product The epoxide ring opening of compound of formula IV may be conducted in the presence of hydrohalic acid followed by acetalisation with aldehyde or ketone to form compound of formula (V). The epoxide ring opening of the compound of Formula IV may be conducted by suitably reacting the compound of Formula IV with a hydrohalic acid selected from the group comprising HF, HCl, HBr etc, preferably HF.

The acetalisation of the compound of Formula IV may be conducted by suitably reacting the compound of Formula III with an aldehyde or ketone selected from the group comprising formaldehyde, paraldehyde, acetone, benzaldehyde, acetophenone, diethylketone, cyclohexane corboxaldehyde sodium metabisulphite complex, cyclopentanone preferably acetone.

In the present invention, the epoxide ring opening of compound of formula IV may be conducted in the presence of hydrohalic acid selected from the group comprising HF, HCl, HBr etc, preferably HF followed by acetalisation with aldehyde or ketone selected from the group comprising formaldehyde, paraldehyde, acetone, benzaldehyde, acetophenone, diethylketone, cyclohexane corboxaldehyde sodium metabisulphite complex, cyclopentanone preferably acetone to form compound of formula (V).

The compound of formula V may be converted to the compound of formula I by deacetylation by reacting with reagents selected from group comprising sodium hydroxide, potassium hydroxide etc. and solvent as methanol, methylene chloride, water or their combination thereof.

Optionally, the debromination of compound of formula IV may be conducted in presence of a catalyst, a thiol compound and an aprotic solvent to obtain the compound of formula VI when R4 in formula VI is H.

In the present invention, catalyst is selected from the group comprising chromous or chromium sulfate, chromous or chromium chloride or its hydrate, preferably chromium chloride hexahydrate. The chromium (III) can be recycled to chromium (II) as is known to those skilled in the art. The means for recycling chromium (III) to chromium (II) includes zinc, magnesium, zinc amalgam and magnesium amalgam. Preferred is zinc and magnesium; most preferred is zinc. It is preferred that when the means for recycling is zinc it be present as zinc dust.

Thiols include compounds of the formula $R_t$—SH (Formula VIII). It is preferred that $R_t$ be —$CH_2$—COOH or —$CH_2CH_2$—COOH; it is more preferred that the thiol be thioglycolic (thiovanic) acid where $R_t$ is —$CH_2$—COOH. Improved chemical yields result from the use of greater than 1 equivalent of the thiol, preferably from about 1.5 to about 3.0 equivalents. In the present invention compound of formula (V) is debrominated to form compound of formula (VI) when R4 in formula VI is H in presence of catalyst, Rt-SH (VIII) with an aprotic solvent at appropriate temperature, wherein $$R_t\text{—SH} \qquad \text{Formula VIII}$$

wherein $R_t$ is —$CH_2COOH$ or —$CH_2CH_2COOH$ preferably $R_t$ is —$CH_2COOH$.

Suitable aprotic solvents include DMF, DMAC, acetone, methylene chloride, THF, acetonitrile, DMSO and mixtures thereof. Alcoholic solvents include methanol, ethanol, isopropanol and butanol. Preferred are DMF and DMSO.

In the present invention, aprotic solvent is selected from the group comprising DMF, DMAC, acetone, methylene chloride, THF, acetonitrile, DMSO and mixtures thereof, preferably DMF and DMSO.

In one embodiment, the compound of formula IV may undergo epoxide ring opening by suitably reacting the compound of Formula IV with a hydrohalic acid selected from the group comprising HF, HCl, HBr etc, preferably HF followed by deacetylation to form the compound of Formula A and optionally purified and utilized for commercial purposes. When on C-16 and C-17 of the compound of formula is "OH", then the compound as (11β, 16α)-9-Fluoro-11, 16, 17, 21-tetrahydroxypregna-1, 4-diene-3, 20-dione (Formula A), also known as Triamcinolone.

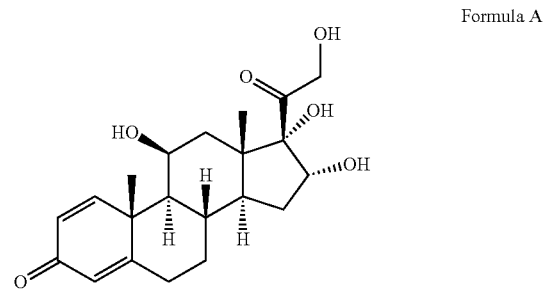

Formula A

In another embodiment of the present invention, the compound of formula (IV) is converted to compound of formula (I) comprising $R_1$ is —$CH_3$, $R_2$ is —$CH_3$, $R_3$ is —$COCH_3$, $R_4$ is —F, $R_6$ is —F by treating with acetone and hydrofluoric acid i.e. Fluocinonide In yet another embodiment of the present invention, the compound of formula (IV) is converted to compound of formula (I) comprising R₁ is —CH₃, R₂ is —CH3, R3 is —H—R₄ is —F, R₆ is —F by treating with acetone and hydrofluoric acid followed by deacetylation with Methanol and Methylene chloride in the presence of sodium hydroxide i.e. Fluocinolone acetonide In yet another embodiment of the present invention, the compound of formula (IV) is converted to compound of formula (I) comprising R₁ is —CH₃, R₂ is —CH3, R3 is —H, is —H, R₆ is —F by treating with acetone and hydrobromic acid followed by sequential step of debromination and deacetylation i.e. Flunisolide.

The compound of formula I may be optionally purified to obtain a pure compound. Such purification may be done by means of crystallization or column chromatography.

Advantages of the Present Invention

1. The process of the present invention uses commonly available and inexpensive materials.
2. The process is simple and does not involve any toxic materials.
3. The process yields several intermediates that have biological activity and commercial utility.

The invention will now be further illustrated by non limiting examples.

WORKING EXAMPLES

Example-1: Process for Preparation of Flunisolide of Formula I from 3TR

Scheme 1: Synthesis of Flunisolide from 3TR

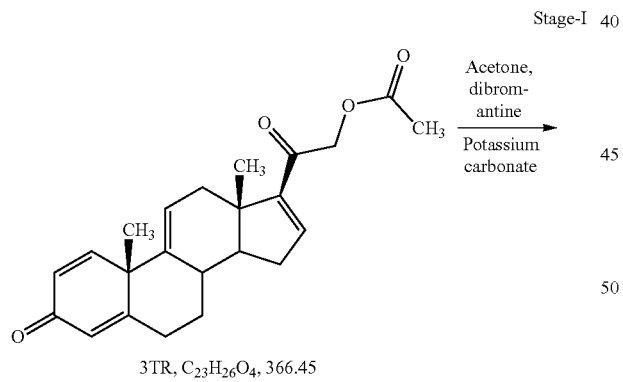

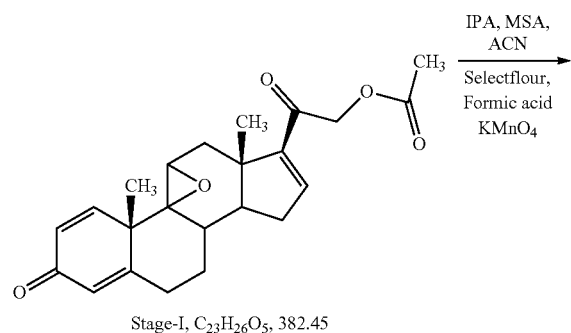

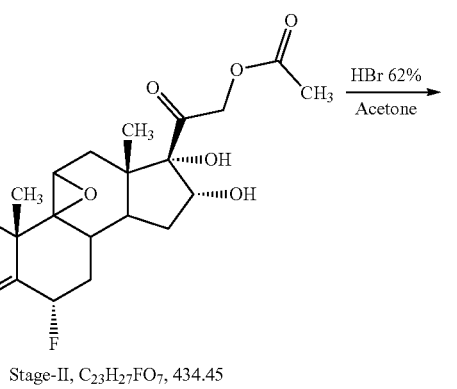

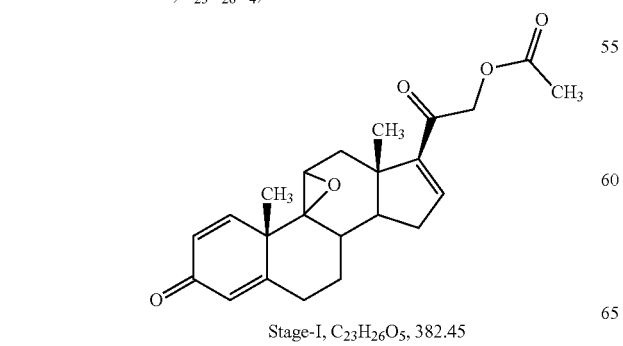

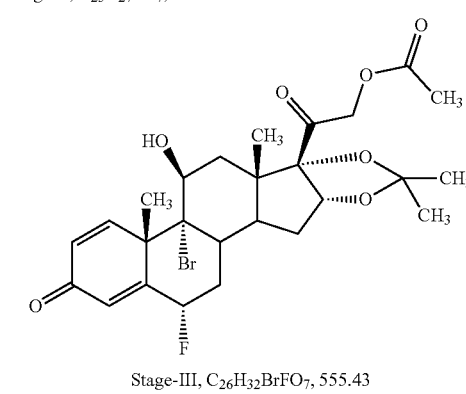

-continued

Stage-IV

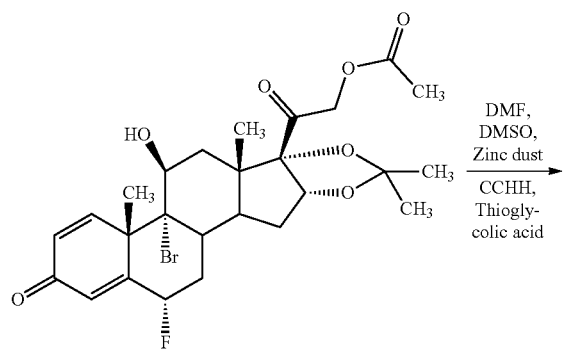

Stage-III, $C_{26}H_{32}BrFO_7$, 555.43

DMF, DMSO, Zinc dust
CCHH, Thioglycolic acid

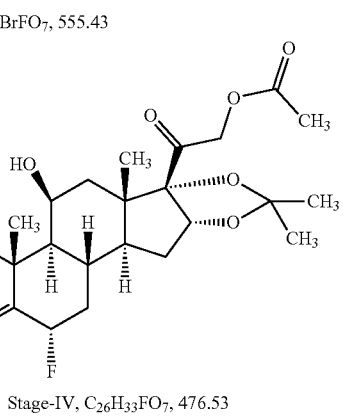

Stage-IV, $C_{26}H_{33}FO_7$, 476.53

Stage-V

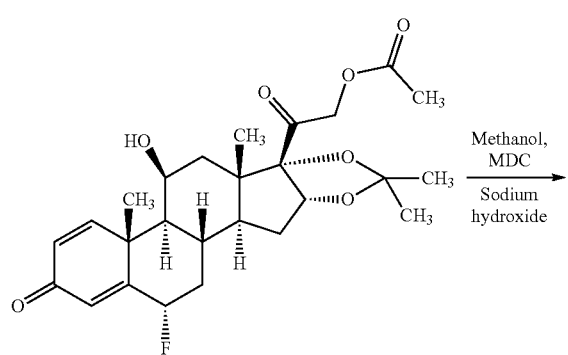

Stage-IV, $C_{26}H_{33}FO_7$, 476.53

Methanol, MDC
Sodium hydroxide

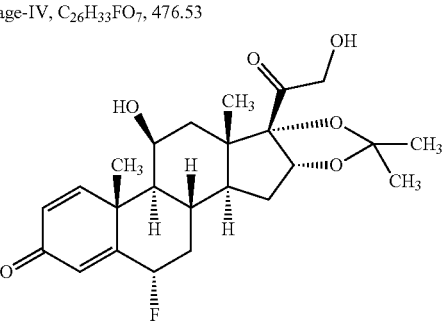

Flunisolide, $C_{24}H_{31}FO_6$, 434.498

Stage-I: (Epoxidation)

Charge 1.30 L of acetone (13.0 volume), 100 gm of 3TR (0.27 mol) in a glass flask, stir till clear solution, cool to −5° C. to −10° C., added 4.0 ml of perchloric acid solution (0.044 mol) in 650 ml purified water (6.5 volume) at −5° C. to −10° C. and added 50 gm of dibromantine (0.18 mol) at same temperature. Stir at −5° C. to −10° C. for 02 hours. In-process check by TLC against 3TR, should be absent. Added 100 gm of potassium carbonate solution (0.72 mol) in 400 ml purified water (4.0 volume) at −5° C. to 0° C., temperature gradually raised up to 35° c.±2° C., stir at same temperature for 12 hours. In-process check by TLC against inter-step, should be absent. Cool to 0° C. to 5° C., added 36 ml of acetic acid (0.63 mol) to neutralized the pH of reaction mass, distill the solvent till thick mass under reduced pressure further added 3.0 L of purified water (30 volume) at 0° C. to 5° C., maintaining the temperature 10° C.±5° C. for 02 hours. Filter and washed with purified water. Dry the wet material at 45° C.±2° C. until the moisture contents less than 0.50%

Output=100 gm
Yield=96%
HPLC Purity=97.1%

Stage-II: (Sequential Steps of Dihydroxylation and Fluorination)

Charge 801 ml of Isopropenyl acetate (9.0 volume), 2.67 ml of methane sulphonic acid (0.04 mol) in a glass flask. Heated to 85° C.±5° C., added 89.0 gm of stage-I (0.23 mol), stir for 03 hours at same temperature. In-process check by TLC against stage-I, should be absent. Cool to 25° C.±5° C. and adjust pH neutral using 4.0 ml of tri ethyl amine (0.03 mol). Recovery of isopropenyl acetate under vacuum at below 60° C. and degassed with 178 ml of acetonitrile (02 volume). Charge 979 ml of acetonitrile (11 volume), cool to −5° C. to −10° C., added 89.0 ml of purified water (1.0 volume) at same temperature, added 89 gm of select fluor (0.25 mol) at −5° C. to −10° C., stir for 12 hours at same temperature. In-process check by TLC against inter step, should be absent. Added 1.1 L of purified water (12.4 volume) at same temperature, Adjust pH neutral using liq. Ammonia at 15° C.±5° C. Charge 445 ml of methylene dichloride (5 volume) at same temperature, stir, settle, separate methylene chloride layer, distill till last drop and degassed with acetone. Charge 5.0 L of acetone (56.18 volume), still till clear solution, cool to −5° C. to −10° C., added 40 ml of formic acid (1.06 mol) and 60 gm of potassium permanganate (0.38 mol) at same temperature, stir for one hour. In-process check by TLC against interstep, should be absent, added 10 gm of sodium meta bisulphite solution (0.053 mol) in 100 ml of water (1.0 volume) at same temperature, temperature raised up to 15° C. and added 30 gm of hyflow super cell, further raised the temperature up to 28° C., stir for one hour, filter the reaction mass and washed with 1.0 L of acetone (11.2 volume). Collect the filtrate in a glass flask and added 10 gm of charcoal activated, stir and filter through hyflow bed and washed with 500 ml of acetone (5.6 volume), collect the total filtrate in a clean glass flask and recover the acetone under vacuum at below 45° C.±5° C. till reaction volume app. 400 ml. Cool to ambient temperature, added 600 ml of purified water (6.7 volume), cool to 0° C. to 5° C., stir for one hour, filter and washed with purified water, wet material dried at 45° C.±5° C. till moisture contents less than 1.0%

Output=100 gm
Yield=98.9%
HPLC Purity=81.35%

Stage-III: (Sequential Steps of Opening of Epoxide Ring with Hydrohalic Acid and Acetalisation with Aldehyde or Ketone)

Charge 25 ml of Hydro bromic acid 62% (0.33 mol) in a glass flask and cool to −5° C. to −10° C., added 5.0 gm of stage-II (0.012 mol) at same temperature, stir for one hour. In-process check by TLC against stage-II, should be absent.

Added 5.0 ml of acetone (1.0 volume) at −10° C.±2° C., stir for one hour. In-process check by TLC against inter step, should be absent. Quenched the reaction mass in 100 ml of chilled purified water (20 volume) at 0° C. to 5° C., stir for 03 hours, filter and washed with purified water till neutral pH, wet material dried at 40° C.±5° C. till moisture content less than 3.0%

Output=5.0 gm
Yield=78.3%
HPLC Purity=88.74%

Stage-IV: (Debromination)

Charge 4.1 ml of N, N-dimethyl form amide (0.82 volume) in a glass flask under argon gas bubbling, added 3.0 ml of N, N-dimethyl sulphoxide (0.60 volume), 0.5 gm of chromium chloride hexahydrate (0.002 mol), 0.58 gm of zinc dust (0.009 mol) at ambient temperature. Cool to −7° C. to −10° C., added 1.91 ml of thioglycolic acid (0.027 mol) at same temperature and added 5 gm of stage-III (0.009 mol) solution in 25 ml of N, N-dimethyl form amide (5 volume) at same temperature, stir for 02 hours. In-process check by TLC against stage-III, should be absent. Reaction mass quenched in 200 ml of purified water (40 volume), stir for one hour at 10° C.±2° C., filtered and washed with purified water, wet material dried at 40° C.±5° C. till moisture content less than 3.0%

Output=3.6 gm
Yield=83.9%
HPLC Purity=80.5%

Stage-V: (Deacetylation)

Charge 30 ml of methanol (10 volume), 30 ml of methylene chloride (10 volume) in a glass flask under argon gas bubbling, added 3.0 gm of stage-IV (0.0063 mol), cool to −5° C.±2° C., added 0.06 gm of sodium hydroxide (0.0015 mol) solution in 3.0 ml of methanol (1.0 volume) at −5° C.±2° C., stir for 02 hours at same temperature. In-process check by TLC against stage-III, should be absent. Adjust pH neutral using 0.09 ml of acetic acid (0.0016 mol), distilled the methanol and methylene chloride mixture under vacuum at below 40° C. till thick mass, cool to ambient temperature and added 9.0 ml of purified water (03 volume), cool to 0° C. to 5° C. and stir for one hour, filter and washed with purified water, wet material dried at 45° C.±5° C. till loss on drying less than 1.0%

Output=2.40 gm
Yield=87.60%
HPLC Purity=98.4
Specific rotation: +104.78°

Example-2: Process for Preparation of Fluocinolone Acetonide of Formula I from 3TR Scheme 2: Synthesis of Fluocinolone acetonide from 3TR

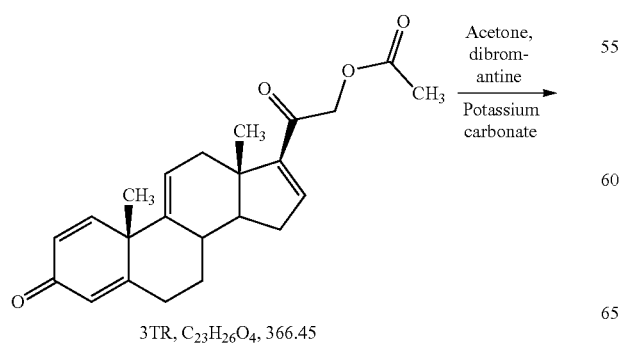

3TR, C$_{23}$H$_{26}$O$_4$, 366.45

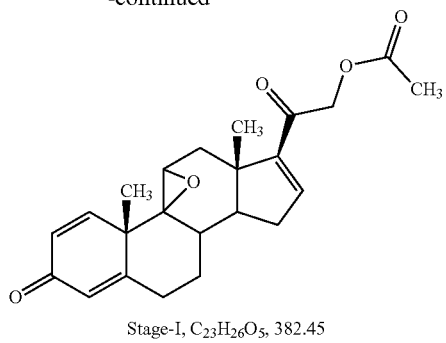

Stage-I, C$_{23}$H$_{26}$O$_5$, 382.45

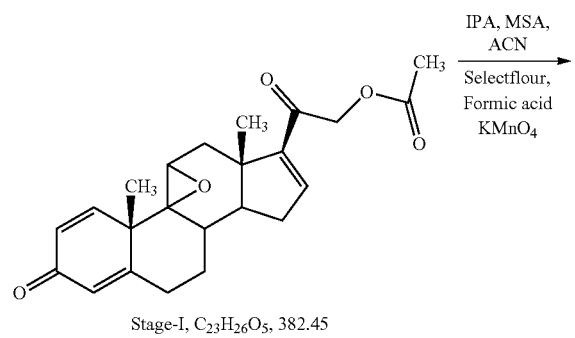

Stage-I, C$_{23}$H$_{26}$O$_5$, 382.45

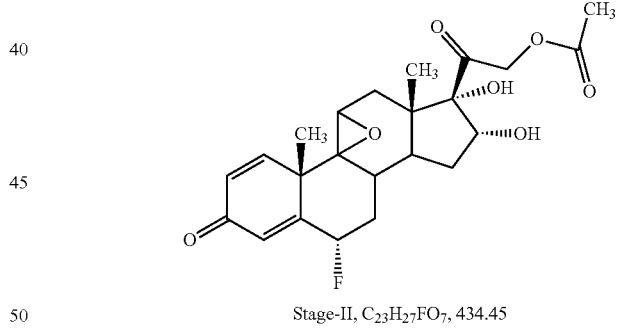

Stage-II, C$_{23}$H$_{27}$FO$_7$, 434.45

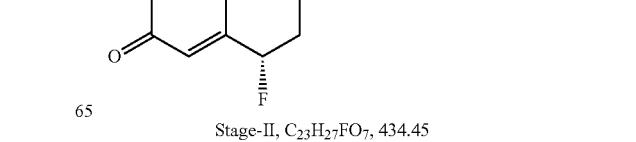

Stage-II, C$_{23}$H$_{27}$FO$_7$, 434.45

-continued

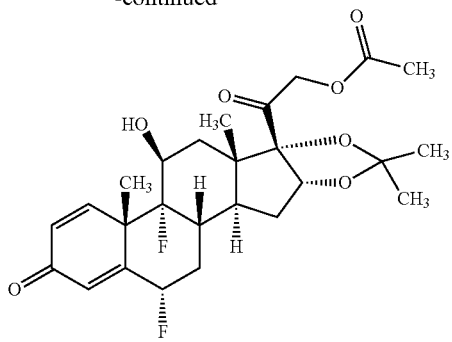

Stage-III, $C_{26}H_{32}F_2O_7$, 494.53

Stage-IV

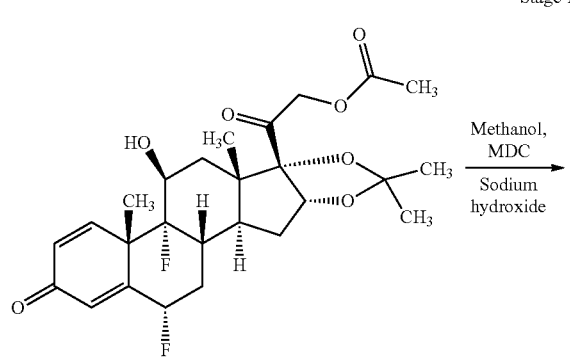

Stage-III, $C_{26}H_{32}F_2O_7$, 494.53

Methanol, MDC
Sodium hydroxide

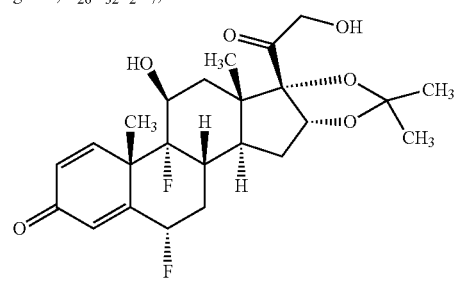

Fluocinolone acetonide, $C_{24}H_{30}F_2O_6$, 452.49

Stage-I: (Epoxidation)

Charge 130 ml of acetone (13.0 volume), 10 gm of 3TR (0.027 mol) in a glass flask, stir till clear solution, cool to −5° C. to −10° C., added 0.4 ml of perchloric acid (0.0044 mol) solution in 65 ml of purified water (6.5 volume) at −5° C. to −10° C. and added 5.0 gm of dibromantine (0.018 mol) at same temperature. Stir at −5° C. to −10° C. for 02 hours. In-process check by TLC against 3TR, should be absent. Added 10 gm of potassium carbonate (0.072 mol) solution in 40 ml of purified water (4.0 volume) at −5° C. to 0° C., temperature gradually raised up to 35° C.±2° C., stir at same temperature for 12 hours. In-process check by TLC against inter-step, should be absent. Cool to 0° C. to 5° C., added 3.6 ml of acetic acid (0.063 mol) to neutralized the pH of reaction mass, distill the solvent till thick mass under reduced pressure further added 0.30 L of purified water (30 volume) at 0° C. to 5° C., maintaining the temperature 10° C.±5° C. for 02 hours. Filter and washed with purified water. Dry the wet material at 45° C.±2° C. until the moisture contents less than 0.50%

Output=10 gm
Yield=96%
HPLC Purity=97.0%

Stage-II: (Sequential Steps of Fluorination and Dihydroxylation)

Charge 81 ml of Isopropenyl acetate (9.0 volume), 0.27 ml of methane sulphonic acid (0.004 mol) in a glass flask. Heated to 85° C.±5° C., added 9.0 gm of stage-I (0.024 mol), stir for 03 hours at same temperature. In-process check by TLC against stage-I, should be absent. Cool to 25° C.±5° C. and adjust pH neutral using 0.40 ml of triethyl amine (0.0029 mol). Recovery of isopropenyl acetate under vacuum at below 60° C. and degassed with 18 ml of acetonitrile (02 volume). Charge 100 ml of acetonitrile (11.1 volume), cool to −5° C. to −10° C., added 9.0 ml of purified water (1.0 volume) at same temperature, added 9 gm of selectfluor (0.025 mol) at −5° C. to −10° C., stir for 12 hours at same temperature. In-process check by TLC against inter step, should be absent. Added 110 ml of purified water (12.2 volume) at same temperature, Adjust pH neutral using liq. Ammonia at 15° C.±5° C. Charge 45 ml of methylene dichloride (5 volume) at same temperature, stir, settle, separate methylene chloride layer, distill till last drop and degassed with acetone. Charge 500 ml of acetone (56.18 volume), still till clear solution, cool to −5° C. to −10° C., added 4.0 ml of formic acid (1.06 mol) and 6.0 gm of potassium permanganate (0.38 mol) at same temperature, stir for one hour. In-process check by TLC against inter step, should be absent, added 1.0 gm of sodium metabisulphite (0.0053 mol) solution in 10 ml of water at same temperature, temperature raised up to 15° C. and added 3.0 gm of hyflow super cell, further raised the temperature up to 28° C., stir for one hour, filter the reaction mass and washed with 100 ml of acetone (11.1 volume). Collect the filtrate in a glass flask and added 1.0 gm of charcoal activated, stir and filter through hyflow bed and washed with 50 ml of acetone (5.6 volume), collect the total filtrate in a clean glass flask and recover the acetone under vacuum at below 45° C.±5° C. till reaction volume app. 40 ml. Cool to ambient temperature, added 60 ml of purified water (6.7 volume), cool to 0° C. to 5° C., stir for one hour, filter and washed with purified water, wet material dried at 45° C.±5° C. till moisture contents less than 1.0%

Output=9.2 gm
Yield=80.96%
HPLC Purity=81.0%

Stage-III: (Sequential Steps of Opening of Epoxide Ring with Hydrohalic Acid and Acetalisation with Aldehyde or Ketone)

Charge 36.8 ml of Hydrofluoric acid 70% (1.52 mol) in a HDPE reactor and cool to −25° C. to −30° C., added 9.2 gm of stage-II (0.021 mol) at −25° C. to −30° C., stir for 04 hours. In-process check by TLC against stage-II, should be absent. Cool to −45° C. to −50° C. and added 5.52 ml of acetone (0.076 mol) at same temperature, stir for 02 hours. In-process check by TLC against inter step, should be absent. Added 18.4 ml of purified water (02 volume) up to 0° C. adjust pH neutral using 147.2 ml of liq. Ammonia (16.0 volume) at 0° C. to 5° C. stir and filter and washed with purified water, wet material dried at 45° C. to 50° C. till moisture content less than 1.0%

Output=8.20 gm
Yield=78.32%
HPLC Purity=80.0%

Purification:

Charge 80 ml of methylene chloride (9.8 volume), 80 ml of methanol (9.8 volume) in a glass flask, added 8.0 gm of stage-III (0.016 mol) and stir till clear solution, added 0.8 gm of charcoal activated, stir for 30 min., filter through hyflow bed and washed with 8.0 ml of methanol and 8.0 ml of methylene chloride mixture, collect the filtrate in a glass flask and distilled to attained the temperature up to 60° C., apply vacuum and distilled till thick mass, cool to 0° C. to 5° C., stir for One hour, filter and washed with 8.0 ml of chilled methanol, wet material dried at 45° C.±5° C. till moisture content less than 1.0%

Output=7.20 gm
HPLC Purity=87.0%

Stage-IV: (Deacetylation)

Charge 70 ml of methanol (10 volume), 70 ml of methylene chloride (10 volume) in a glass flask under argon gas bubbling, added 7.0 gm of stage-III (0.014 mol), cool to −5° C.±2° C., added 0.14 gm of sodium hydroxide (0.0035 mol) solution in 7.0 ml of methanol at −5° C.±2° C., stir for 02 hours at same temperature. In-process check by TLC against stage-III, should be absent. Adjust pH neutral using 0.21 ml of acetic acid (0.0037 mol), distilled the methanol and methylene chloride mixture under vacuum at below 40° C. till thick mass, cool to ambient temperature and added 10.5 ml of purified water (1.5 volume), cool to 0° C. to 5° C. and stir for one hour, filter and washed with purified water, wet material dried at 45° C.±5° C. till moisture content less than 1.0%

Output=3.25 gm
Yield=50.78%
HPLC Purity=90.0%

Stage-V: (Purification)

Charge 30 ml of methylene chloride (10 volume), 30 ml of methanol (10 volume) in a glass flask, added 3.0 gm of stage-IV (0.0066 mol) and stir till clear solution, added 0.3 gm of charcoal activated, stir for 30 min., filter through hyflow bed and washed with 3.0 ml of methanol and 3.0 ml of methylene chloride mixture, collect the filtrate in a glass flask and distilled to attained the temperature up to 60° C., apply vacuum and distilled till thick mass, cool to 0° C. to 5° C., stir for one hour, filter and washed with 3.0 ml of chilled methanol, wet material dried at 45° C.±5° C. till loss on drying less than 1.0%

Output=1.20 gm
HPLC Purity=88.7%
Specific rotation: +108.51°

Further purification required to achieve purity of >98% with desired solvent.

Example-3: Process for Preparation of Fluocinonide of Formula a from 3TR

Scheme 3: Synthesis of Fluocinonide from 3TR

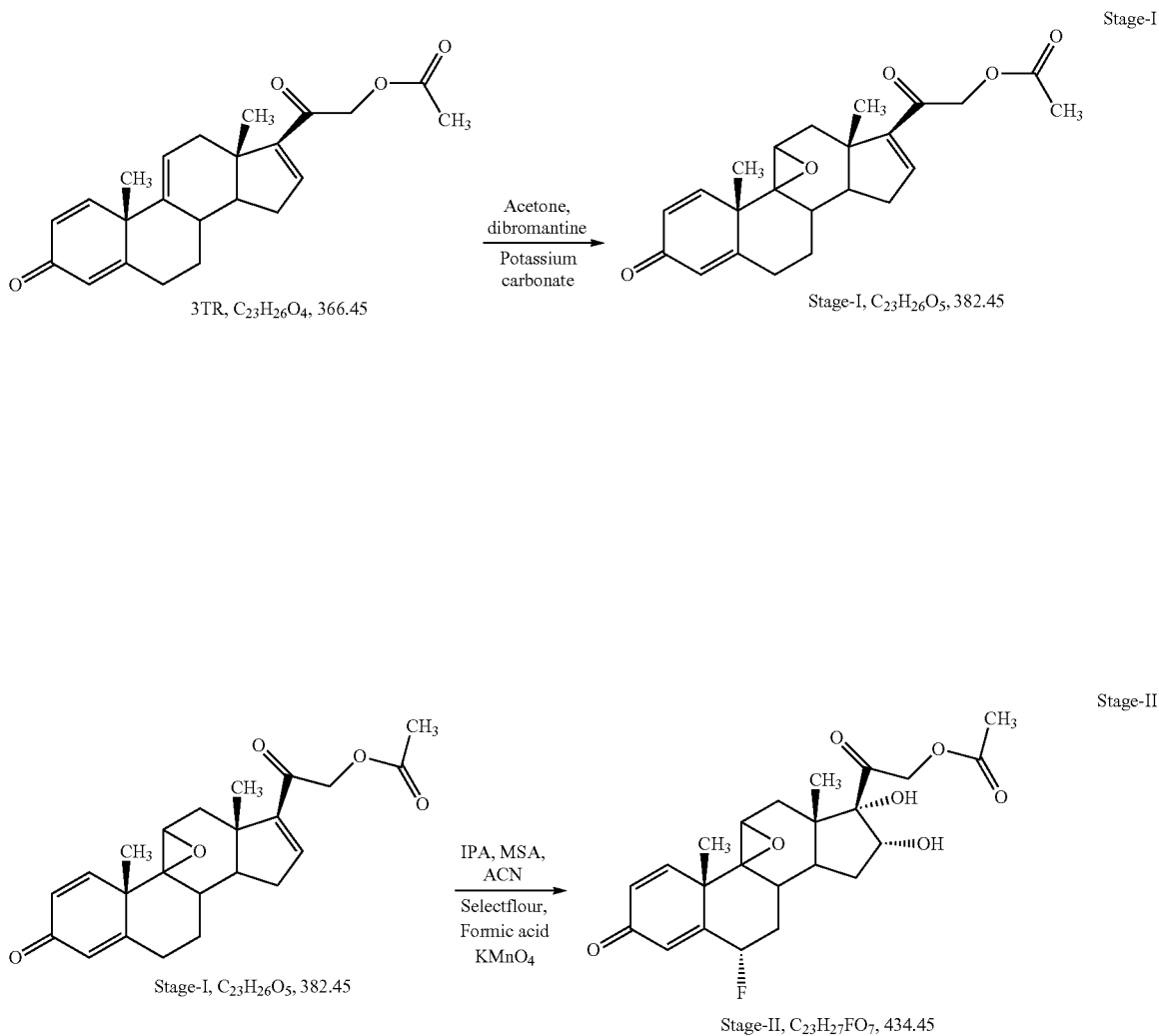

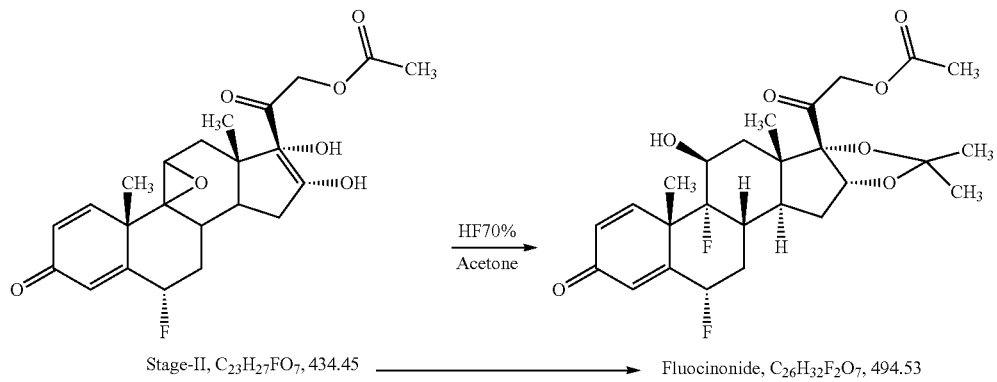

Stage-II, $C_{23}H_{27}FO_7$, 434.45 →(HF 70%, Acetone)→ Fluocinonide, $C_{26}H_{32}F_2O_7$, 494.53 — Stage-III Stage-I: (Epoxidation)

Charge 130 ml of acetone (13.0 volume), 10 gm of 3TR (0.027 mol) in a glass flask, stir till clear solution, cool to −5° C. to −10° C., added 0.4 ml of perchloric acid (0.0044 mol) solution in 65 ml purified water (6.5 volume) at −5° C. to −10° C. and added 5.0 gm of dibromantine (0.018 mol) at same temperature. Stir at −5° C. to −10° C. for 02 hours. In-process check by TLC against 3TR, should be absent. Added 10 gm of potassium carbonate (0.072 mol) solution in 40 ml purified water (4.0 volume) at −5° C. to 0° C., temperature gradually raised up to 35° C.±2° C., stir at same temperature for 12 hours. In-process check by TLC against inter-step, should be absent. Cool to 0° C. to 5° C., added 3.6 ml of acetic acid (0.063 mol) to neutralized the pH of reaction mass, distill the solvent till thick mass under reduced pressure further added 0.30 L of purified water (30 volume) at 0° C. to 5° C., maintaining the temperature 10° C.±5° C. for 02 hours. Filter and washed with purified water. Dry the wet material at 45° C.±2° C. until the moisture contents less than 0.50%

Output=10 gm
Yield=96%
HPLC Purity=97.0%

Stage-II: ((Sequential Steps of Fluorination and Dihydroxylation)

Charge 81 ml of Isopropenyl acetate (9.0 volume), 0.27 ml of methane sulphonic acid (0.004 mol) in a glass flask. Heated to 85° C.±5° C., added 9.0 gm of stage-I (0.024 mol), stir for 03 hours at same temperature. In-process check by TLC against stage-I, should be absent. Cool to 25° C.±5° C. and adjust pH neutral using 0.40 ml of tri ethyl amine (0.003 mol). Recovery of isopropenyl acetate under vacuum at below 60° C. and degassed with 18 ml of acetonitrile (02 volume). Charge 100 ml of acetonitrile (11.0 volume), cool to −5° C. to −10° C., added 9.0 ml of purified water (1.0 volume) at same temperature, added 9 gm of selectfluor (0.025 mol) at −5° C. to −10° C., stir for 12 hours at same temperature. In-process check by TLC against inter step, should be absent. Added 110 ml of purified water (12.2 volume) at same temperature, Adjust pH neutral using liq. Ammonia at 15° C.±5° C. Charge 45 ml of methylene dichloride (5 volume) at same temperature, stir, settle, separate methylene chloride layer, distill till last drop and degassed with acetone. Charge 500 ml of acetone (56.18 volume), still till clear solution, cool to −5° C. to −10° C., added 4.0 ml of formic acid (1.06 mol) and 6.0 gm of potassium permanganate (0.38 mol) at same temperature, stir for one hour. In-process check by TLC against inter step, should be absent, added 1.0 gm of sodium meta bisulphite (0.0053 mol) solution in 10 ml of water (1.1 volume) at same temperature, temperature raised up to 15° C. and added 3.0 gm of hyflow super cell, further raised the temperature up to 28° C., stir for one hour, filter the reaction mass and washed with 100 ml of acetone (11.1 volume). Collect the filtrate in a glass flask and added 1.0 gm of charcoal activated, stir and filter through hyflow bed and washed with 50 ml of acetone (5.6 volume), collect the total filtrate in a clean glass flask and recover the acetone under vacuum at below 45° C.±5° C. till reaction volume app. 40 ml. Cool to ambient temperature, added 60 ml of purified water (6.7 volume), cool to 0° C. to 5° C., stir for one hour, filter and washed with purified water, wet material dried at 45° C.±5° C. till moisture contents less than 1.0%

Output=8.2 gm
Yield=80.24%
HPLC Purity=81%

Stage-III (Sequential Steps of Opening of Epoxide Ring with Hydrohalic Acid and Acetalisation with Aldehyde or Ketone)

Charge 32.0 ml of Hydrofluoric acid 70% (1.32 mol) in a HDPE reactor and cool to −25° C. to −30° C., added 8.0 gm of stage-II (0.018 mol) at −25° C. to −30° C., stir for 04 hours. In-process check by TLC against stage-II should be absent. Cool to −45° C. to −50° C. and added 4.8 ml of acetone (0.066 mol) at same temperature, stir for 02 hours. In-process check by TLC against inter step, should be absent. Added 12.0 ml of purified water (1.5 volume) up to 0° C. adjust pH neutral using 128.0 ml of liq. Ammonia (16 volume) at 0° C. to 5° C. stir and filter and washed with purified water, wet material dried at 45° C. to 50° C. till moisture content less than 1.0%

Output=3.52 gm
Yield=38.68%
HPLC Purity=80%
Purification:

Charge 30 ml of methylene chloride (10 volume), 30 ml of methanol (10 volume) in a glass flask, added 3.0 gm of stage-III (0.006 mol) and stir till clear solution, added 0.3 gm of charcoal activated, stir for 30 min., filter through hyflow bed and washed with 3.0 ml of methanol and 3.0 ml of methylene chloride mixture, collect the filtrate in a glass flask and distilled to attained the temperature up to 60° C., apply vacuum and distilled till thick mass, cool to 0° C. to 5° C., stir for One hour, filter and washed with 3.0 ml of chilled methanol, wet material dried at 45° C.±5° C. till loss on drying less than 1.0%

Output=1.50 gm
HPLC Purity=96%
Specific rotation: +86.96°

We claim:

1. A novel process for the preparation of pregnadiene derivatives of formula I and stereoisomers and intermediates thereof

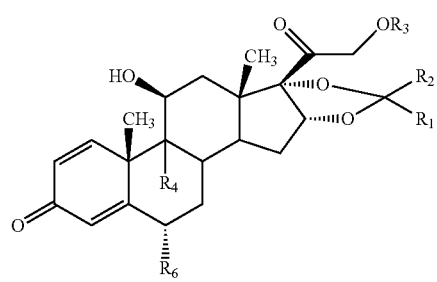

Formula I wherein:
R₁ and R₂ are independently hydrogen or C1-C8 straight, branched alkyl chain, saturated or unsaturated cycloalkyl;
R₃ is hydrogen or

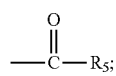

R₅ is C1-C8 straight, branched alkyl chain or cycloalkyl;
R₄ and R₆ are independently hydrogen or halogen;
comprising the steps of:
i. epoxidation of compound of formula II to obtain 9,11-oxido derivative of compound of formula III

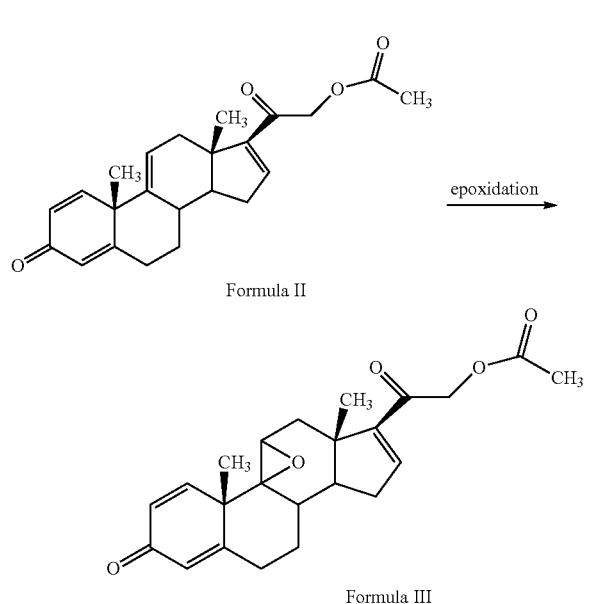

i. dihydroxylation and optional fluorination of compound of formula III to obtain compound of formula IV wherein R₆ is fluorine

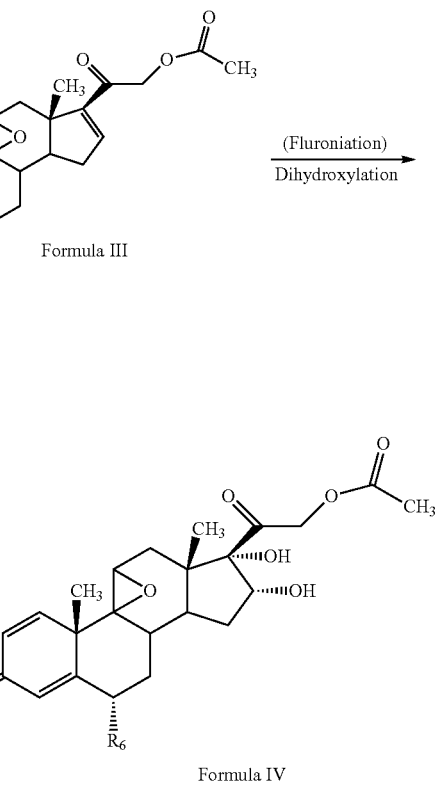

ii. epoxide ring opening of compound of formula IV followed by acetalisation in the presence of hydrohalic acid to with debromination of R₄ from being bromine to hydrogen to obtain the compound of formula V

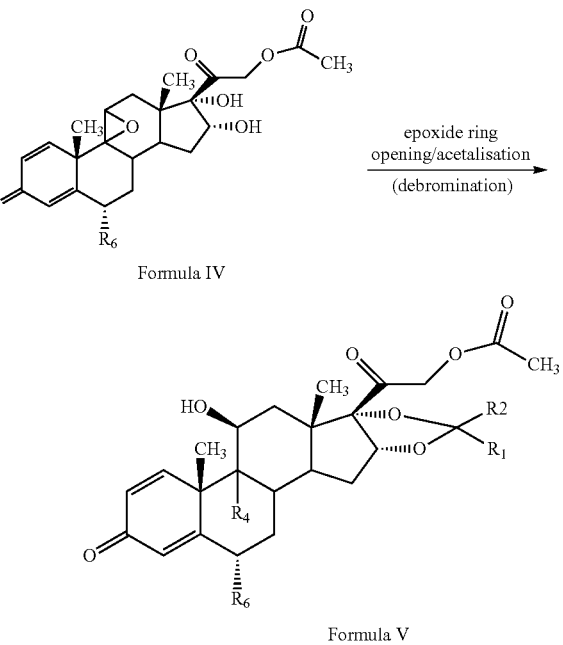

iv. deacetylation of compound of Formula V to obtain compound of formula I

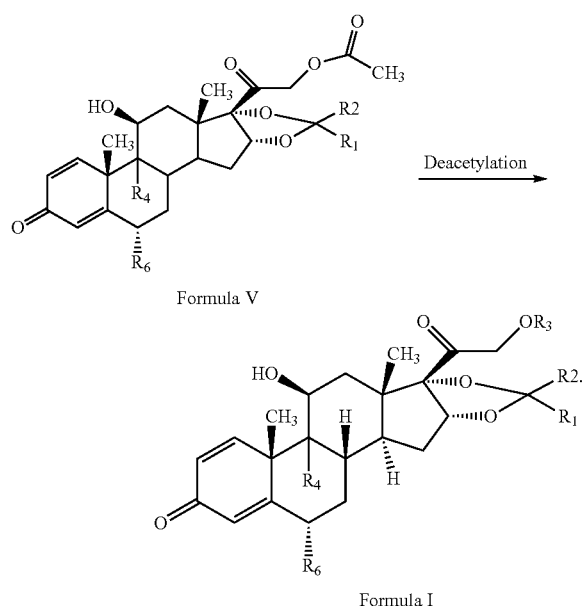

Formula V

Formula I

2. The process as claimed in claim 1, wherein the compound of Formula (1) is
   i. (1S,2S,4R,8S,9S,11S,12R,13S,19S)-12,19-difluoro-11-hydroxy-8-(2-hydroxyacetyl)-6,6,9,13-tetramethyl-5,7-dioxapentacyclo[10.8.0.02,9.04,8.013,18]icosa 14,17-dien-16-one;
   ii. $6_\alpha$, 9-difluoro: 11β,16α,17,21-tetrahydroxypregna-1,4-diene-3,20-dione, cyclic 16,17-acetal with acetone,21-acetate;
   iii. 1S,2S,4R,8S,9S,11S,12S,13R,19S)-19-fluoro-11-hydroxy-8-(2-hydroxyacetyl)-6,6,9,13-tetramethyl-5,7-dioxapentacyclo[10.8.0.02,9.04,8.013,18]icosa-14,17-dien-16-one;
   iv. (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one
   v. 2-[(1S,2S,4R,8S,9S,11S,12R,13S)-12'-fluoro-11'-hydroxy-9',13'-dimethyl-16'-oxo-5',7'-dioxaspiro[cyclopentane-1,6' pentacyclo[10.8.0.02,9.04,8.013,18] icosane]-14',17'-dien-8'-yl]-2-oxoethyl acetate;
   vi. (11β,16α)-9-Fluoro-11,16,17,21-tetrahydroxypregna-1,4-diene-3,20-dione;
   vii. (11β,16α)-21-(3,3-Dimethyl-1-oxobutoxy)-9-fluoro-11-hydroxy-16,17-((1 methylethylidene)bis(oxy)) pregna-1,4-diene-3,20-dione.

3. The process as claimed in claim 1, wherein the epoxidation is carried out with an epoxidizing agent with Perchloric acid and an alkali, wherein the expodizing agent is selected from the group consisting of dibromantin, N-bromoacetaminde or N-bromosuccinimide and the alkali is selected from the group consisting of potassium carbonate, sodium or potassium hydroxide or their carbonates or acetate.

4. The process as claimed in claim 1, wherein the fluorination is carried out with fluorinating agent selected from the group consisting of N-fluoro-benzene sulfonamide, N-fluoro-N chloromethyltrimethylene diamine bistetrafluoroborateSelectfluoro, 1-fluoropyridinium triflate, 1-fluoropyridinium tetrafluoroborate, or 1-fluoropyridinium pyridine heptafluorodiborateetc, preferably Selectfluor® and the solvent selected from the group consisting of acetonitrile, isopropenyl acetate, dichloromethane, dimethyl formamide, diethyl ether, isopropenylacetate, and tetrahydrofuran.

5. The process as claimed in claim 1, wherein the dihydroxylation is carried out with an oxidizing agent selected from the group consisting of potassium permanganate, potassium dichromate, chromic acid, peroxyacids, formic acid or mixtures thereof.

6. The process as claimed in claim 1, wherein the epoxide ring opening is carried out in the presence of a hydrohalic acid and selected from the group consisting of HF, HCl, HBr and acetalisation is carried out with aldehyde or ketone selected from the group consisting of formaldehyde, paraldehyde, acetone, benzaldehyde, acetophenone, diethylketone, cyclohexane corboxaldehyde sodium metabisulphite complex, cyclopentanone.

7. The process as claimed in claim 1, wherein the deacetylation is carried out with sodium hydroxide or potassium hydroxide and a solvent selected from the group consisting of methanol, methylene chloride, water or a combination thereof.

8. The process as claimed in claim 1, wherein the debromination is carried out in the presence of a catalyst selected from the group consisting of comprising chromous or chromium sulfate, chromium chloride hexahydrate, chromous or chromium chloride or its hydrate, a thiol compound of the formula Rt-SH (Formula VIII), wherein Rt is —CH2COOH or —CH2CH2COOH and an aprotic solvent selected from the group consisting of DMF, DMAC, acetone, methylene chloride, THF, acetonitrile, DMSO and mixtures thereof and alcoholic solvents selected from the group selected from the group consisting of methanol, ethanol, isopropanol and butanol.

* * * * *

UNITED STATES PATENT AND TRADEMARK OFFICE
CERTIFICATE OF CORRECTION

PATENT NO. : 10,538,551 B2  
APPLICATION NO. : 16/327972  
DATED : January 21, 2020  
INVENTOR(S) : Vinayak Tripathi et al.

Page 1 of 1

It is certified that error appears in the above-identified patent and that said Letters Patent is hereby corrected as shown below:

In the Claims

Claim 4, Lines 12-13 – replace "bistetrafluoroborateSelectfluoro" with ---bistetrafluoroborate, Selectfluoro---, Claim 8, Line 40 – replace "consisting of comprising chromous" with ---"consisting of chromous"---.

Signed and Sealed this  
Tenth Day of March, 2020

Andrei Iancu  
*Director of the United States Patent and Trademark Office*